United States Patent [19]

Deschamps et al.

[11] Patent Number: 4,460,553

[45] Date of Patent: Jul. 17, 1984

[54] PROCESS FOR THE HYDRODESULFURIZATION OF NATURAL GAS CONTAINING ORGANIC SULFUR COMPOUNDS AND OXYGEN

[75] Inventors: André Deschamps, Noisy le Roi; Jean Cosyns, Maule; Jean-François Le Page, Rueil-Malmaison, all of France

[73] Assignee: Institut Francais du Petrole, Rueil-Malmaison, France

[21] Appl. No.: 466,690

[22] Filed: Feb. 15, 1983

[30] Foreign Application Priority Data

Feb. 15, 1982 [FR] France .................................. 82 02550

[51] Int. Cl.³ ............................................. B01D 53/36
[52] U.S. Cl. ..................................... 423/219; 423/244; 423/245; 423/564
[58] Field of Search .................. 423/219, 230, 244 R, 423/245 S, 210 S, 224, 563, 564; 502/262, 333

[56] References Cited

U.S. PATENT DOCUMENTS 4,181,503  1/1980  Lesieur et al. .................. 423/650 X

FOREIGN PATENT DOCUMENTS 340016  12/1930  United Kingdom ............ 423/244 R

*Primary Examiner*—Earl C. Thomas
*Attorney, Agent, or Firm*—Millen and White

[57] ABSTRACT

Process for hydrodesulfurizing a gas comprising together methane, at least one organic sulfur compound and oxygen, characterized by the step of passing a mixture of said gas with a hydrogen containing gas on a palladium catalyst at a temperature of 300° to 450° C.

The gas usually comprises at least 2 mg/Nm³ of sulfur as organic sulfur and 0.05 to 2% by volume of oxygen.

7 Claims, No Drawings

PROCESS FOR THE HYDRODESULFURIZATION OF NATURAL GAS CONTAINING ORGANIC SULFUR COMPOUNDS AND OXYGEN

The invention relates to a process for the hydrodesulfurization of natural gas containing organic sulfur compounds and oxygen.

Natural gas, as distributed by a pipeline network, contains traces of organic sulfur compounds either resulting from an incomplete desulfurization or voluntarily introduced to give a smell to the gas (usually tetrahydrothiophene or THT). Although present in the gas at a low concentration (for example 10 to 30 mg THT per Normal cubic meter of gas), these sulfur compounds are a nuisance when the gas is used in the presence of sulfur-sensitive catalysts. It is specially the case when the gas is used to manufacture hydrogen or synthesis gas by steam reforming, for example in ammonia or methanol producing plants.

The gas is usually desulfurized by hydrogen treatment in the presence of a hydrodesulfurization catalyst to convert the organic sulfur compounds to hydrogen sulfide which can be easily separated or retained by, for example, a zinc oxide mass. The catalysts to be used in the hydrodesulfurization step usually comprise cobalt and molybdenum or nickel and molybdenum on an alumina carrier.

The network gas sometimes also contains small amounts of air added to adjust the combustion value of excessively rich gases. The oxygen content is usually from 0.05 to 1% by volume. The hydrodesulfurization catalysts do not work properly in these conditions: a portion of sulfur is converted to elemental sulfur and/or sulfur dioxide which are not retained by the zinc oxide mass and poison the catalysts used in the subsequent treatment of the gas.

To obviate this disadvantage, it has already been proposed, as disclosed in U.S. Pat. No. 4,181,503, to first eliminate oxygen by adding hydrogen to the gas and treating the mixture with a platinum-containing catalyst, and then, in a second step, to treat the oxygen-free gas with a hydrodesulfurization catalyst containing nickel and molybdenum to convert the organic sulfur to hydrogen sulfide. This process necessitates the use of two catalysts and is costly.

It has now been discovered, and this is the object of the invention, that these two operations can be performed in one step by using a palladium-containing catalyst under the following conditions:

According to the process of the invention, a gas containing more than 2 mg/Nm$^3$, for example 2 to 20 mg/Nm$^3$, more usually 4 to 12 mg/Nm$^3$ of sulfur in the form of organic sulfur compounds and 0.05 to 2% by volume, usually 0.1 to 1% by volume of oxygen, is treated with a hydrogen-containing gas at a temperature from 300° to 450° C., preferably 345° to 400° C., on a palladium-containing catalyst.

The hydrogenation gas may consist of relatively pure hydrogen or, more advantageously, of an industrial gas comprising both hydrogen and carbon monoxide.

Catalysts for use in the invention comprise 0.1 to 5% b.w. of palladium deposited on (or incorporated in) a carrier such as, for example, alumina or silica, the specific surface of the carrier (BET method) being preferably from 5 to 400 m$^2$/g. Any appropriate method can be used to incorporate palladium, such as: impregnation with an aqueous solution of a palladium compound, for example an aqueous solution of a nitrate, a chloride or an amine complex of the Pd (NH$_3$)$_4$X$_2$ type (X being an anion) or a solution of an organic complex such as palladium acetylacetonate dissolved in an appropriate organic compound.

After impregnation, the palladium compound is treated in any appropriate manner to obtain the reduced metal, for example by calcination in air followed with hydrogen-reduction. Prior to its use, the catalyst can also be treated with a mixture of hydrogen and a sulfur compound such as, for example, H$_2$S.

The space velocity, i.e. the gas volume (under normal conditions of temperature and pressure) treated per volume of catalyst per hour, is between 500 and 10,000, more generally between 1000 and 5000.

The hydrogen amount is at least equal to the theoretical amount necessary to convert the organic sulfur compounds to hydrogen sulfide and to convert oxygen to steam. It amounts preferably to two times this quantity, and usually to 2 to 6% by volume of the natural gas amount.

The operating pressure may vary widely, for example between 1 and 80 bars. The preferred operating pressure is that of the pipeline network or of the process utilizing the gas, particularly between 20 and 60 bars.

Natural gas means a methane-containing gas, for example natural gas properly said or the associated gas from an oil well. The process also concerns the treatment of synthetic methane.

The organic sulfur compounds to be eliminated by the process of the invention are, for example:
tetrahydrothiophene
mercaptans of the formula R—SH where R=hydrocarbyl of 1-6 carbon atoms, for example methylmercaptan, ethylmercaptan, propylmercaptans and butylmercaptans,
sulfides of the formula R$_1$R$_2$S where R$_1$ and R$_2$ are each hydrocarbyl of 1-4 carbon atoms, for example methyl sulfide, ethyl sulfide and butyl sulfide,
disulfides of the formula R$_1$SSR$_2$ where R$_1$ and R$_2$ are each hydrocarbyl of 1-4 carbon atoms, for example dimethyldisulfide, diethyldisulfide and dipropyldisulfide.

EXAMPLE

The following non-limitative example is given to illustrate the invention.

The performance of a commercial catalyst, containing cobalt and molybdenum (14% MoO$_3$ and 3% of CoO) on alumina, has been compared, in a laboratory plant, to that of a palladium-containing catalyst prepared as follows:

An alumina carrier of a 70 m$^2$/g specific surface and a 0.6 cc/g pore volume is impregnated with a palladium nitrate solution, so as to obtain 0.3% b.w. of palladium metal in the final catalyst. After impregnation, the catalyst is dried and then calcined at 450° C. for 2 hours in an air stream. Before use, the catalyst is reduced for 2 hours at 200° C. in a hydrogen stream.

The gas to be treated is natural gas consisting essentially of methane and comprising 25 mg/Nm$^3$ of tetrahydrothiophene (THT) and 0.5% by volume of oxygen.

100 cc of each of the above described catalysts is placed in an electrically heated tubular steel reactor of 3 cm internal diameter. 500 Nl/h of natural gas and 15 Nl/h of hydrogen are injected at the top of the reactor under a pressure of 30 bars.

The gas discharged from the bottom of the reactor is expanded and analyzed to determine its THT, H₂S, SO₂, sulfur and oxygen contents.

The following Table gives the results obtained with the above two catalysts, at different temperatures, after a starting period of 100 hours.

It is found that the use of the palladium catalyst results in an almost complete conversion of THT to hydrogen sulfide in the temperature interval from 300° to 400° C., more particularly from 350° to 400° C. Conversely the cobalt-molybdenum catalyst yields at any temperature a gas containing traces of hydrogen sulfide, sulfur dioxide and elemental sulfur. This probably results from the fact that the evolved gas always contains oxygen. Moreover, at each temperature increase, a temporary increase of the sulfur dioxide content is observed, probably attributable to the oxidation of the cobalt and molybdenum sulfides of the catalyst.

| CATALYST | T °C. | THT mg/Nm³ | H₂S mg/Nm³ | SO₂ mg/Nm³ | S mg/Nm³ | ppm Vol. |
|---|---|---|---|---|---|---|
| Pd/Al₂O₃ | 250 | nd | 4 | 9 | 1 | 200 |
| | 300 | nd | 9 | 1 | 0.1 | 15 |
| | 350 | nd | 9.65 | nd | nd | nd |
| | 400 | nd | 9.63 | nd | nd | nd |
| CoMo/Al₂O₃ | 250 | 15 | 1 | 4 | 0.8 | 4800 |
| | 300 | 5 | 3 | 6.5 | 1.5 | 4500 |
| | 350 | nd | 1 | 16.1 | 0.5 | 4100 |
| | 400 | nd | 2 | 13 | 1 | 1200 | nd = not detected

What is claimed is:

1. A process for hydrodesulfurizing a gas (A) comprising together methane, at least one organic sulfur compound and oxygen, characterized by the step of passing a mixture of said gas with a hydrogen containing gas on a palladium catalyst at a temperature of 300° to 450° C.

2. A process according to claim 1, wherein the gas (A) comprises at least 2 mg/Nm³ of sulfur as organic sulfur compound and 0.05 to 2% by volume of oxygen.

3. A process according to claim 2, wherein the gas (A) comprises from 2 to 20 mg/Nm³ of sulfur as organic sulfur compound.

4. A process according to claim 1, wherein the temperature is from 345° to 400° C.

5. A process according to claim 1, wherein the hydrogen amount is at least the theoretical amount necessary to convert the organic sulfur compound to hydrogen sulfide and to convert oxygen to steam.

6. A process according to claim 1, wherein the hydrogen amount represents 2 to 6 % by volume of the gas (A).

7. A process according to claim 1, wherein the catalyst comprises from 0.1 to 5% by weight of palladium on alumina or silica.

* * * * *